United States Patent [19]

Chupp et al.

[11] 4,242,123

[45] Dec. 30, 1980

[54] HERBICIDAL COMPOSITION AND METHOD OF USE

[75] Inventors: John P. Chupp, Kirkwood; Jimmy W. Worley, Creve Coeur, both of Mo.

[73] Assignee: Monsanto Company, St. Louis, Mo.

[21] Appl. No.: 965,354

[22] Filed: Nov. 30, 1978

[51] Int. Cl.³ ............................................. A01N 37/44
[52] U.S. Cl. ........................................ 71/111; 560/47
[58] Field of Search ................................... 71/111, 118

[56] References Cited

U.S. PATENT DOCUMENTS

| 2,921,077 | 1/1960 | Hiltmann et al. | 560/19 |
|---|---|---|---|
| 3,100,226 | 8/1963 | Raman et al. | 71/118 |
| 3,371,106 | 2/1968 | Berliner et al. | 71/118 |
| 3,403,994 | 10/1968 | Olin | 71/118 |
| 3,636,078 | 1/1972 | Pawloski | 71/111 |
| 3,871,865 | 3/1975 | Teach | 260/562 B |
| 3,928,416 | 12/1975 | Bayer et al. | 71/118 |
| 4,135,050 | 1/1979 | Hess et al. | 560/47 |

*Primary Examiner*—Glennon H. Hollrah
*Attorney, Agent, or Firm*—Patricia A. Coburn; Donald W. Peterson

[57] ABSTRACT

The disclosure herein relates to herbicidal compositions containing 2'-carboalkoxy-6'-alkyl-2-haloacetanilides and method of use to selectively control undesired vegetation in agricultural crops, e.g., monocotyledons such as wheat, sorghum and rice and dicotyledons such as sugarbeets and soybeans.

5 Claims, No Drawings

HERBICIDAL COMPOSITION AND METHOD OF USE

BACKGROUND OF THE INVENTION

The invention herein pertains to the field of herbicidal compositions and method of use thereof. In more particular, the herbicidal compositions herein have particular application in the control of undesired plants associated with monocotyledons such as wheat, sorghum and rice and dicotyledons such as sugarbeets and soybeans.

DESCRIPTION OF THE PRIOR ART

It is known in the prior art to prepare 2-haloacetanilides having a variety of substituents on the phenyl ring and on the anilide nitrogen atom.

As relevant to the compounds used in the present invention various 2'-carboalkoxy-6'-alkyl-N-substituted anilides and 2-haloacetanilides are known. For example, U.S. Pat. No. 2,921,077 discloses the use of 2-carbomethoxy-6-methyl-N-chloroacetanilide as an intermediate in the preparation of the corresponding N-diethylamino acetanilide. However, the latter products are useful as local anesthetics and no other utility is disclosed for said intermediate.

U.S. Pat. No. 3,636,078 discloses the use of herbicidal 2-propynyl ester of N-acetyl anthranilic acid as an inhibitor of broadleaf bean growth at 50 lbs/acre (56 kg/hectare); no other herbicidal utility is disclosed.

Various other less-relevant prior art discloses other esters of N-substituted anthranilic acid useful in non-herbicidal utilities.

SUMMARY OF THE INVENTION

The present invention relates to herbicidal compositions containing 2'-carboalkoxy-6'-alkyl-2-haloacetanilides as the active ingredient and herbicidal method of use, particularly to control noxious weeds in sugarbeets, soybeans, wheat, sorghum and rice.

In more particular, the compounds used as active ingredients in the herbicidal compositions of this invention are those having the formula

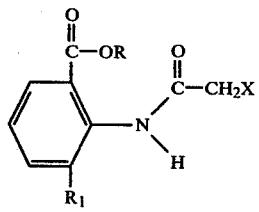

wherein X is halogen, particularly chlorine, bromine or iodine and, preferably chlorine and R and $R_1$ are independently $C_{1-10}$ lower alkyl, preferably $C_{1-5}$ lower alkyl and especially methyl. Unless otherwise indicated, "alkyl" is used generically to include primary, secondary and tertiary alkyl radicals.

Representative compounds of the present invention include those in which the R and $R_1$ groups of the above formula include methyl, ethyl, propyl, isopropyl, n-butyl, primary isobutyl, secondary isobutyl, tertiary butyl, n-amyl, branch chain amyls, the normal and branched hexyls, heptyls, octyls, nonyls, and decyls.

The preferred compounds used as active ingredients in the herbicidal compositions of the present invention are those in which X is chlorine, bromine or iodine and, in particular chlorine, and R and $R_1$ are $C_{1-10}$ alkyl, preferably the $C_{1-5}$ alkyls.

The specific compound of preference is 2'-carbomethoxy-6'-methyl-2-chloroacetanilide.

The herbicidal compositions herein are useful as selective herbicides by applying them to the locus of undesirable plants to be controlled and desirable plants to be protected.

The invention will be more clearly understood by reference to the following detailed description of specific examples thereof. In these examples and throughout the specification, all proportions are expressed in part by weight unless otherwise indicated.

DETAILED DESCRIPTION OF THE INVENTION

EXAMPLE 1

This example describes the preparation of 2'-carbomethoxy-6'-methyl-2-chloroacetanilide.

To a stirred mixture of 1.1 g ($6.7 \times 10^{-3}$ mol) methyl 3-methylanthranilate in 50 ml methylene chloride and 50 ml 10% aqueous sodium carbonate at 3° C. with stirring was added 0.08 ml ($10^{-2}$ mol) of chloroacetyl chloride in about one minute. The cooling bath was removed and the mixture stirred one hour. The two layers were separated and the aqueous phase extracted with two 20 ml portions of methylene chloride. The combined organic layers were washed with two 20 ml portions of water, dried over $MgSO_4$ and concentrated to 1.2 g of white solid product (75% yield); mp 79°–81° C.

Analysis calculated for $C_{11}H_{12}ClNO_3$.

|    | Calc'd | Found |
|----|--------|-------|
| C  | 54.67  | 54.53 |
| H  | 5.01   | 5.11  |
| Cl | 14.67  | 14.77 |

EXAMPLES 2 to 46

The compounds in the following examples may also be prepared by substantial repetition of the general procedure set forth in the foregoing example, modified as to reaction temperatures, times, solvent, etc., to account for the nature of the particular reactants, as will be apparent to those skilled in the art. In the examples, the individual compounds are those whose members are identified by the general formula

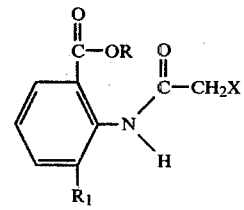

| Example | R | $R_1$ | X |
|---------|---|-------|---|
| 2 | methyl | ethyl | Cl |
| 3 | methyl | n-propyl | Cl |
| 4 | methyl | n-butyl | Cl |
| 5 | methyl | t-butyl | Cl |
| 6 | methyl | amyl | Cl |
| 7 | methyl | hexyl | Cl |
| 8 | methyl | heptyl | Cl |
| 9 | methyl | octyl | Cl |

-continued

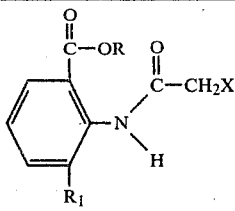

| Example | R | R₁ | X |
|---|---|---|---|
| 10 | methyl | i-propyl | Br |
| 11 | methyl | nonyl | Cl |
| 12 | methyl | decyl | Cl |
| 13 | ethyl | methyl | Cl |
| 14 | ethyl | ethyl | Cl |
| 15 | ethyl | n-propyl | Cl |
| 16 | ethyl | i-propyl | Br |
| 17 | ethyl | n-butyl | Br |
| 18 | ethyl | t-butyl | Cl |
| 19 | ethyl | amyl | Cl |
| 20 | ethyl | octyl | Cl |
| 21 | ethyl | decyl | Cl |
| 22 | ethyl | ethyl | Br |
| 23 | n-propyl | methyl | Cl |
| 24 | n-propyl | ethyl | Cl |
| 25 | n-propyl | ethyl | Br |
| 26 | n-propyl | n-propyl | Br |
| 27 | i-propyl | methyl | Cl |
| 28 | i-propyl | ethyl | Cl |
| 29 | i-propyl | propyl | Cl |
| 30 | i-propyl | t-butyl | Cl |
| 31 | t-butyl | methyl | Cl |
| 32 | t-butyl | ethyl | Br |
| 33 | t-butyl | n-propyl | Cl |
| 34 | t-butyl | t-butyl | Cl |
| 35 | t-amyl | methyl | Br |
| 36 | t-amyl | ethyl | I |
| 37 | t-amyl | n-propyl | Cl |
| 38 | t-amyl | i-propyl | Cl |
| 39 | t-amyl | t-butyl | Cl |
| 40 | ethyl | methyl | I |
| 41 | ethyl | ethyl | I |
| 42 | i-propyl | i-propyl | I |
| 43 | t-butyl | methyl | I |
| 44 | methyl | methyl | Br |
| 45 | methyl | ethyl | Br |
| 46 | ethyl | i-propyl | I |

In order to illustrate the advantage of the present invention, the selective preemergence herbicidal activity of the preferred species of this invention, i.e., the compound of Example 1, representative of 2'-carboalkoxy-6'-alkyl-2-haloacetanilides, was determined in greenhouse tests on soybeans, sugarbeets, wheat, rice and sorghum and selected weed plants.

The pre-emergent data were obtained as follows:

A good grade of top soil was placed in aluminum pans and compacted to a depth of three-eighths to one-half inch (9.53–12.7 mm) from the top of the pan. On top of the soil was placed a predetermined number of seeds or vegetables propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth. Approximately 2 weeks after seeding and treating, the plants were observed and the results recorded. The herbicidal rating was obtained by means of a fixed scale based on the percent injury of each plant species. The ratings are defined as follows:

| % Control | Rating |
|---|---|
| 0–24 | 0 - No injury |
| 25–49 | 1 - Slight injury |
| 50–74 | 2 - Moderate injury |
| 75–100 | 3 - Severe injury |

Following the above procedure, the compound of Example 1 was tested at application rates of 5 lb/acre (5.6 kg/ha) and 1.0 lb/acre (1.12 kg/ha) against selected weeds in the above crops. At 5.0 lb/acre (5.6 kg/ha) said compound exhibited no injury to the crops soybeans, sugarbeets, wheat, rice or sorghum, but caused severe injury to panicum, barnyardgrass and crabgrass, and slight-to-moderate injury to lambsquarters and downy brome. Even at 1.0 lb/acre (1.12 kg/ha) the compound of Example 1 caused severe injury to barnyardgrass and crabgrass and moderate injury to panicum.

In other tests at 5.0 lb/acre, the compound of Example 1 was also found to exhibit severe injury to nutsedge and slight injury to velvet leaf.

The selective preemergence data set forth above clearly illustrate the efficacy of the preferred compound representative of the present invention as a selective herbicide useful in the control of undesirable weeds in the presence of such agricultural crops as sugarbeets, soybeans, wheat, sorghum and rice.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and polymethylene bis-naphthalenesulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 95 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor of anti-foaming agent or both.

Aqueous suspensions may be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones.

The aqueous suspensions and emulsifiable oil compositions generally contain from about 5 to 95 parts (preferably 5–50 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredients adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely-divided clays such as kaolin clays, hydrated attapulgite or bentonitic clays. These extenders are sprayed or blended with the active ingredient to form the herbicidal granules.

The granular compositions of this invention generally contain from about 5 parts to about 30 parts by weight of active ingredient per 100 parts by weight of clay and 0 to about 5 parts by weight of surface active agent per 100 parts by weight of particulate clay. The preferred granular compositions contain from about 10 parts to about 25 parts by weight of active ingredient per 100 parts by weight of clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, other acetanilides, uracils, acetic acid or phenol derivatives, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy) phenyl-N,N-dimethylurea
1,1'-dimethyl-4,4'-bipyridinium dichloride
isopropyl N-(3-chlorophenyl) carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2', 1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
2'-methyl-6'-ethyl-N-(2-methoxyprop-2-yl)-2-chloroacetanilide
monosodium acid methanearsonate
disodium methanearsonate
N-(1,1-dimethylpropynyl)-3,5-dichlorobenzamide N-(phosphonomethyl)glycine and its $C_{1-6}$ monoalkyl amine and alkali metal salts and combinations thereof in ratios of 1–4 lb/acre (1.12–4.48 kg/ha) to 1–10 lb/acre of other herbicidal compounds of this invention.

Fertilizers useful in combination with the active ingredients include for example ammonium nitrate, urea, potash, and superphosphate. Other useful additaments include materials in which plant organisms take root and grow such as compost manure, humus, sand and the like.

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above example, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance of media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

We claim:

1. A herbicidal composition comprising an inert adjuvant and an effective amount of a compound of the formula

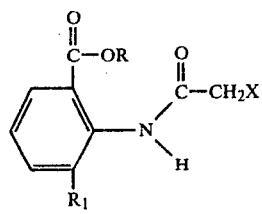

wherein X is chlorine and R and $R_1$ are independently $C_{1-5}$ alkyl.

2. Composition according to claim 1 wherein R and $R_1$ are methyl and X is chloro.

3. A method for controlling undesirable vegetation which comprises applying to the locus thereof a herbicidal composition comprising an inert adjuvant and an effective amount of a compound of the formula

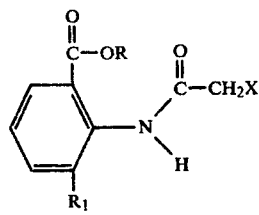

wherein X is chlorine and R and $R_1$ are independently $C_{1-5}$ alkyl.

4. Method according to claim 3 wherein R and $R_1$ are methyl and X is chloro.

5. Method according to claim 4 wherein said composition is applied to weed plants associated with crop plants selected from the group consisting of soybeans, sugarbeets, wheat, rice and sorghum.

* * * * *